US006341230B1

(12) United States Patent
Koike et al.

(10) Patent No.: US 6,341,230 B1
(45) Date of Patent: Jan. 22, 2002

(54) BIOMEDICAL ELECTRODE

(75) Inventors: Yasuaki Koike; Takayuki Kawasaki; Shigehiro Nishiwaki, all of Tokyo; Tadashi Matsumoto; Hideo Akita, both of Osaka, all of (JP)

(73) Assignees: Nihon Kohoen Corporation, Tokyo; Kabushikikaisya Kyoma, Osaka, both of (JP)

( * ) Notice: Subject to any disclaimer, the term of this patent is extended or adjusted under 35 U.S.C. 154(b) by 0 days.

(21) Appl. No.: 09/534,566

(22) Filed: Mar. 27, 2000

(30) Foreign Application Priority Data

Mar. 25, 1999 (JP) ............................................. 11-081322

(51) Int. Cl.$^7$ ............................................. A61B 5/0408
(52) U.S. Cl. ........................ 600/392; 600/394; 607/149; 607/152
(58) Field of Search ................................. 600/391, 392, 600/394; 607/149, 152, 153

(56) References Cited

U.S. PATENT DOCUMENTS 3,774,592 A * 11/1973 Lahr ........................... 600/392
3,993,049 A * 11/1976 Kater ........................... 600/391

FOREIGN PATENT DOCUMENTS

JP          7-445     1/1995    ........... A61F/13/02

* cited by examiner

Primary Examiner—Lee Cohen
(74) Attorney, Agent, or Firm—Sughrue, Mion, Zinn, Macpeak & Seas, PLLC

(57) ABSTRACT

A gel layer retained in a retaining member 15, such as non-woven fabric, is placed on one side of an electrode element 1. The electrode element 1 is held by a flexible and extendable tape 11, and the tape 11 adheres to a biological surface tissue. When being plastered onto the biological surface tissue, the tape 11 is covered with cover films 12 and 13, thereby preventing occurrence of a kink in the tape 11. After the tape 11 has been attached to the biological surface tissue, a butt-joined portion between two sub-divisions constituting a cover film 12 is exfoliated to the outside, thus preventing removal of the tape 11.

7 Claims, 3 Drawing Sheets

BIOMEDICAL ELECTRODE

BACKGROUND OF INVENTION

1. Field of the Invention

The present invention relates to a biomedical electrode which senses a bioelectric signal when adhering to a surface of living tissue (hereinafter referred to as "biological surface tissue"), and more particularly, to a biomedical electrode which easily follows the motion of biological surface tissue and is less likely to cause inflammation.

2. Related art

A disposable biomedical electrode integrally consisting of an electrode element and adhesive tape for fixing the electrode element on biological surface tissue has bee used widely in the field of, for example, an electrocardiograph. FIG. 7 shows the configuration of an example of a prevailing biomedical electrode.

In FIG. 7, an electrode element 1 is made of Ag/AgCl and consists of a disk 1a and a pin 1b integrally protruding from the center of one surface of the disk 1a. A sponge 3 filled with a conductive gel or paste is bonded to the surface of the disk 1a opposite the surface having the pin 1b provided thereon.

Adhesive tape 4 is formed from nonwoven fabric into a tear-drop shape, a circular shape, or a rectangular shape, and a circular opening 4a is formed in the center of the adhesive tape 4. The disk 1a of the electrode element 1 is inserted into the opening 4a. A disk-shaped label 5 is bonded to one surface of the adhesive tape 4. Further, the pin 1b of the electrode element 1b is inserted into a small hole 5a formed in the center of the label 5. In this state, the electrode element 1 is firmly fixed on the label 5 and adheres to biological surface tissue of a subject by way of a strong adhesive layer formed on the surface of the adhesive tape 4 having the label 5 fixed thereon. As a result, there can be minimized noise, which would otherwise be caused by motion of the subject or swinging of a lead wire connected to the pin 1b of the electrode element 1.

When a biomedical electrode is not in use, the surface of the adhesive tape 4 having an adhesive placed thereon is covered with a gel cover 6, thereby preventing mutual adhesion of biomedical electrodes or drying of gel when the biomedical electrode is to be reserved for a long period of time. The outer dimension of the gel cover 6 is greater than that of the adhesive tape 4, and an indentation 6a is formed in the center of the gel cover 6 for accommodating the sponge 3. When a biomedical electrode is used, the gel cover 6 is detached from the adhesive tape 4, thereby uncovering the sponge 3.

In the prevailing biomedical electrode having such a structure, the adhesive tape 4 is made of nonwoven fabric or foam and has a thickness of 1 mm or thereabouts and is comparatively rigid. If the subject performs unnatural motion, the skin may expand and contract or form a kink, thereby causing warpage between the plastered adhesive tape 4 and the surface of the skin. Particularly, such warpage is likely to arise in the outer circumferential portion of the adhesive tape 4, and a corresponding portion of the skin is liable to suffer inflammation.

SUMMARY OF INVENTION

The present invention has been conceived in view of such a backdrop and is aimed at providing a biomedical electrode which facilitates handling of a tape for fixing an electrode element on biological surface tissue, enables the tape to easily follow the motion of the biological surface tissue, and prevents occurrence of inflammation in the portion of the biological surface tissue to which the electrode element adheres.

Accordingly, the present invention provides a biomedical electrode including an electrode element which has at one end thereof a conductive gel layer, and tape which retains the other end of the electrode element and is to be plastered to biological surface tissue, wherein the tape is made of a flexible, extendable, and thin film, and a reinforcing cover film for removably covering the side of the tape opposite the surface to be plastered on the biological surface tissue is provided on the tape.

Preferably, extending the tape to a length which is twice the length of the tape when no tension is applied thereto requires a force of 400 grams or less per 1 cm width.

Preferably, the tape has a steam permeability of 400 $g/m^2/24$ hr or more.

Preferably, the tape has a thickness of 0.1 mm or less.

Preferably, the cover film is divided into two sub-sections, and the butt faces of the two sub-sections are butt-joined. The portion of the cover film in the vicinity of the butt-joined portion is not crimped onto the tape.

Preferably, a cut is formed in the cover film from its center to outer edge. A tab tape for removing a cover film is attached to one side or both sides of the cover film with reference to the cut.

Preferably, a tab tape for removing a cover film is attached to the outer edge of the cover film.

Since the tape which retains an electrode element and is to be plastered on biological surface tissue is made of a flexible, extendable, and thin film, the tape can extend so as to follow the motion of the skin stemming from the movement of the subject, thereby preventing occurrence of inflammation in the skin, which would otherwise be caused when strain is applied to the skin. Since a reinforcing cover film is attached to the tape, no kink arises in the surface of the tape, which would otherwise be caused when a thin tape is plastered on the biological surface tissue.

After the tape has been plastered on the biological surface tissue, a cover film is exfoliated by means of the cover film being removed from the tape and from a butt-joined portion of the cover film toward the outside, thus enabling removal of only the cover film without involvement of exfoliation of the tape.

The tab tape for removing a film is picked up and pulled manually toward the outer edge, thus enabling removal of the cover film from the tape.

The tab tape is manually picked up and pulled upward, thus enabling removal of the cover film from the tape.

DETAILED DESCRIPTION OF PREFERRED EMBODIMENTS

Figure 1:
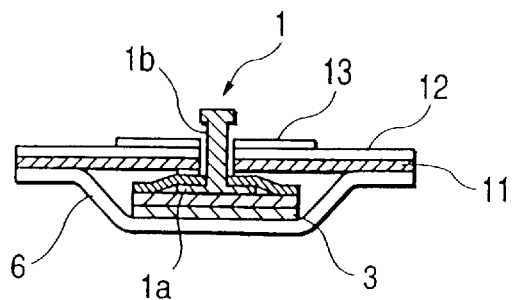
FIG. 1 is a longitudinal cross-sectional view showing the structure of a biomedical electrode according to a first embodiment of the present invention.
Figure 2:
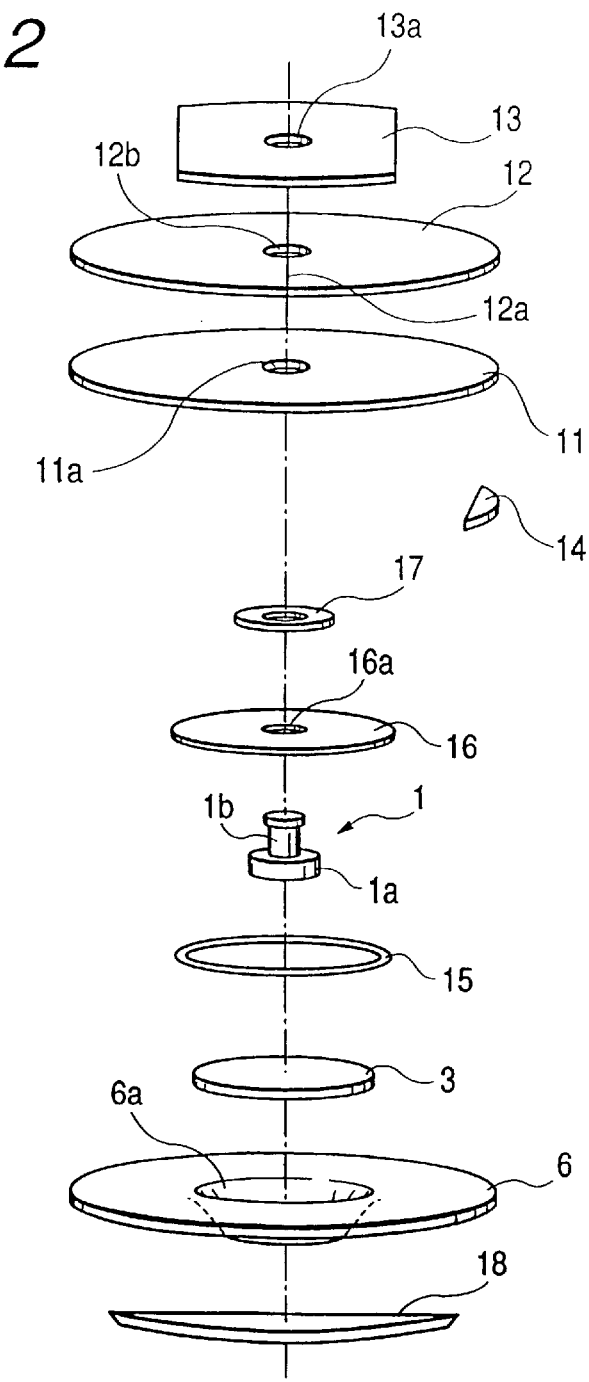
FIG. 2 is an exploded perspective view showing the biomedical electrode shown in FIG. 1.
Figure 7:
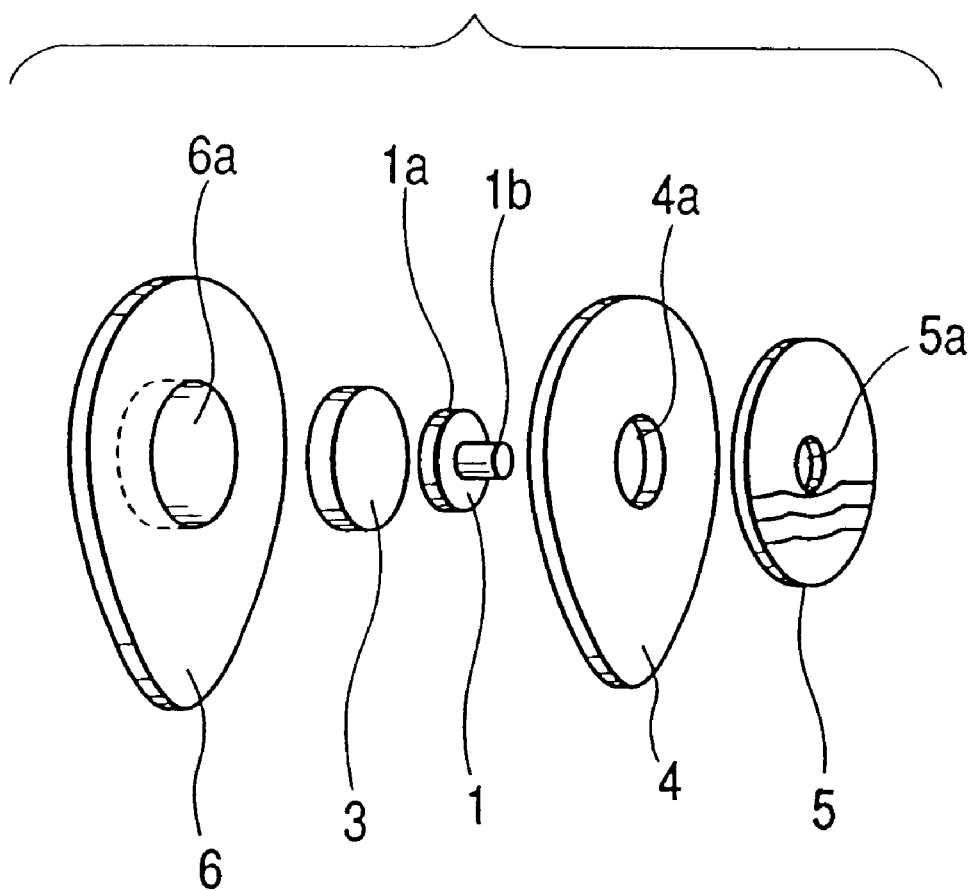
FIG. 7 is an exploded perspective view showing an example structure of a prevailing biomedical electrode.

Biomedical electrodes according to embodiments of the present invention will be described hereinbelow by reference to accompanying drawings. FIG. 1 is a longitudinal cross-sectional view showing an example configuration of a biomedical electrode according to a first embodiment of the present invention, and FIG. 2 is an exploded perspective view showing the biomedical electrode of the first embodiment. Those elements corresponding to those of the prevailing biomedical electrode shown in FIG. 7 are assigned the same reference numerals, and repetition of their explanations is omitted, as necessary.

In FIGS. 1 and 2, a tape 11 fixedly adhering to a biological surface tissue of a subject retaining an electrode element 1 is formed into a circular shape from a flexible and extendable tape, for example, an urethane film. The tape 11 has a thickness of 0.1 mm or less; for example, 0.02 through 0.05 mm. Extending the tape to a length which is twice the length of the tape when no tension is applied thereto requires a force of 400 grams or less per 1 cm width; for example, a force of 200 grams or less. The tape has a steam permeability of 400 g/m$^2$/24 hr or more; for example, a steam permeability of 800 g/m$^2$/24 hr or thereabouts. A pressure-sensitive adhesive layer is placed on one surface of the tape 11.

A first cover film 12—which is formed from a PET film or an OPP film and into a disk shape substantially identical with the tape 11—is crimped onto the surface of the tape opposite the surface having the pressure-sensitive tape provided thereon. The strength of the adhesive force between the first cover film 12 and the tape 11 is made smaller than the strength of the adhesive force between the adhesive layer of the tape 11 and an object to which the tape 11 adheres, so that the first cover film 12 can be readily exfoliated. The first cover film 12 is divided, substantially along the diameter thereof, into two-subdivisions. The portion of the cover film 12 in the vicinity of a butt-joined portion 12a where the butt surfaces of the two sub-divisions are butt-joined is not crimped onto the tape 11. The cover film 12 can be readily exfoliated by means of the cover film 12 being removed from its butt-joined portion toward the outside. A second cover film 13 of rectangular shape having a non-adhesive section provided on both sides thereof or on one side thereof adheres to the outward-facing surface of the first cover film 12. A semicircular tab tape 14 is removably attached to the outer edge of the surface of the tape 11 having the adhesive-layer provided thereon.

A conductive gel layer 3 is provided on the undersurface of the disk 1a of the electrode element 1, and the shape of the gel layer 3 is maintained while being fitted into a circular retaining member 15 made of nonwoven fabric. A disk-shaped label 16 is attached to the upper surface of the disk 1a, and a pin 1b of the electrode element 1 penetrates through a small hole 16a formed in the center of the label 16, thus protruding outwardly. The disk 1a of the electrode element 1 is sandwiched between the label 16 and the retaining member 15, and the label 16 adheres to the outer edge of the retaining member 15, thus enabling reliable contact between the electrode element 1 and the gel layer 3.

The tip end of the pin 1b of the electrode element 1 protruding from the center of the label 16 penetrates through a small hole 11a formed in the center of the tape 11, a small hole 12b formed in the center of the first cover film 12, and a small hole 13a formed in the center of the second cover film 13, thus protruding outwardly. When the biomedical electrode is preserved, the gel layer 3 is covered with the gel cover 6, as in the case of the prevailing biomedical electrode shown in FIG. 7, thus preventing drying of the gel layer 3. The tab tape 14 is temporarily bonded to the outer edge of the tape 11. Further, the gel cover 6 is usually formed from a transparent plastic sheet. In order to make the gel cover 6 noticeable after the gel cover 6 has been exfoliated from the tape 11, an arc-shaped gel cover tape 18 is bonded to or printed along the outer edge of the gel cover 6.

Next will be described procedures for plastering the biomedical electrode of the present embodiment onto the biological surface tissue of a living body. A non-adhesive section of the tab tape 14 is picked up so as to remove the gel cover 6 from the tape 11, thus uncovering the gel layer 3. The tape 11 whose disk-shaped geometry is maintained by means of the cover films 12 and 13 is plastered onto a predetermined location on the biological surface tissue of a subject, so that the electrode element 1 is fixed on the biological surface tissue by way of the gel layer 3. After the second cover film 13 has been exfoliated from the first cover film 12, the two semicircular sub-sections of the first cover film 12 are pulled outwardly while the butt-joined portion 12a of the first cover film 12 which is not bonded to the tape 11 is picked up.

In the present embodiment, since the tape 11 is reinforced by the cover films 12 and 13, the tape 11 can reliably adhere to the biological surface tissue without involvement of a twist or kink arising in the surface of the tape, which would otherwise be caused when a thin tape 11 is plastered on the biological surface tissue, the cover film 12 is exfoliated from the tape 11 and from the butt-joined portion 12a toward the outside, thus preventing removal of the tape 11. Since the tape 11 is made of a flexible, extendable, and thin film the tape can extend so as to follow the motion of the skin stemming from the movement of the subject, thereby preventing occurrence of inflammation in the skin. Since inflammation does not arise in the skin and the tape 11 is made of non-fabric, the edge of the tape 11 is prevented from irritating to the skin.

FIGS. 3 through 6 illustrate the configurations of biomedical electrodes according to the second and third embodiments of the invention. Throughout the drawings, those elements corresponding to those employed in the first embodiment shown in FIGS. 1 and 2 are assigned the same reference numerals, and repetition of their explanations is omitted, as necessary. The biomedical electrodes according to the second and third embodiments are characterized by the structure of a cover film. In other respects, the biomedical electrodes of the second and third embodiments are identical in structure with that of the first embodiment.

Figure 3:
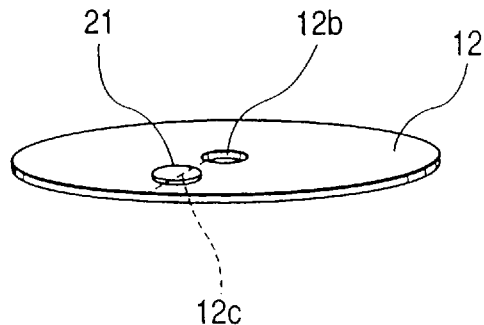
FIG. 3 is a perspective view showing the structure of a cover film of a biomedical electrode according to a second embodiment of the present invention.

FIG. 3 is a perspective view showing the structure of the cover film 12 according to the second embodiment. A cut 12c is formed in the cover film 12 so as to radially extend from the center small hole 12b to the outer edge. A disk-shaped tab tape 21 for removing a film is attached to the cut 2c. The tab tape 21 is attached to one side of the cover film 12 with reference to the cut 12c but not to the remaining side of the cover film 12. The strength of the adhesive force between the tab tape 21 and the cover film 12 is made stronger than the strength of the adhesive force between the cover film 12 and the tape 11 shown in FIG. 2.

According to the second embodiment, a non-bonded portion of the tab tape 21 of the cover film 12 is manually pulled up in a circumferential direction, thus enabling easy exfoliation of the cover film 12 from the tape 11. The force of exfoliation acts on the cover film 12 in its circumferential direction, thus preventing removal of the tape 11. In the first embodiment, after the removal of the second cover film 13 from the first cover film 12, the first cover film 12 is exfoliated from the tape 11. Thus, removing the first cover film 12 from the tape 11 requires two actions in the first embodiment and only one action in the second embodiment.

Figure 4:
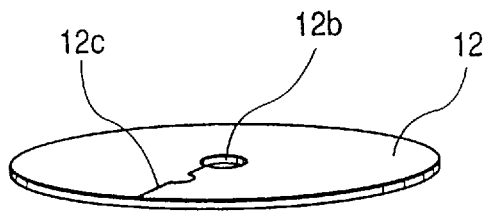
FIG. 4 is a perspective view showing the structure of a modification of the second embodiment shown in FIG. 3.

Although the second embodiment has described a case where the tab tape 21 is formed from another member, a portion of the cut 12c is formed into a semi-circular shape, as shown in FIG. 4, and only the undersurface of the portion of the cut 12c may be so as not to adhere to the tape 11.

Figure 5:
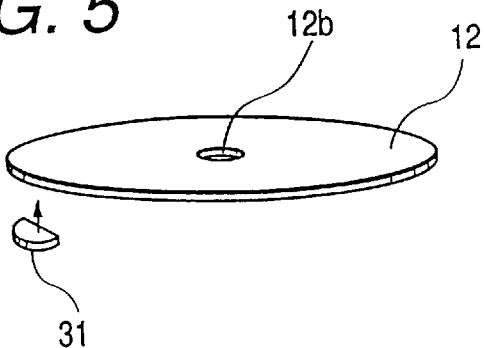
FIG. 5 is a perspective view showing the structure of a cover film of a biomedical electrode according to a third embodiment of the present invention.
Figure 6:
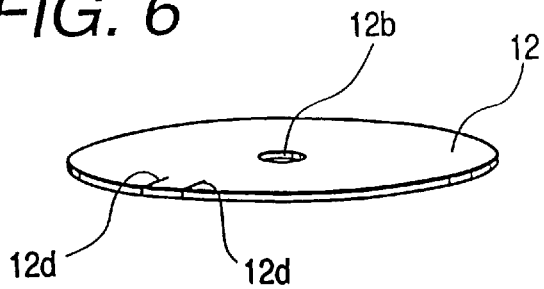
FIG. 6 is a perspective view showing the structure of a modification of the biomedical electrode shown in FIG. 5.

FIG. 5 is a perspective view showing the structure of the cover film 12 according to the third embodiment. A portion of a semicircular tab tape 31 for removing a film is attached to a portion of the outer edge of the cover film 12. The tab tape 31 may be attached to either one of the surfaces of the cover film 12. The strength of the adhesive force between the tab tape 31 and the cover film 12 is made stronger than the strength of the adhesive force between the cover film 12 and the tape 11 shown in FIG. 2.

According to the third embodiment, the tab tape 31 of the cover film 12 is manually pulled upwardly, thus enabling easy exfoliation of the cover film 12 from the tape 11. At this time, the tape 11 is also pulled upward together with removal of the cover film 12. However, the electrode element 11 for detecting a bioelectric signal is supported in the center of the tape 11, thus posing no problem.

Although the third embodiment has described a case where the tab tape 31 is formed from another member, a pair of cuts 12d are formed in a portion of the outer edge of the cover film 12, as shown in FIG. 4, and no adhesive may be applied to only the undersurface of the portion of the cover film 12 located between the cuts 12d.

As has been described above, in the biomedical electrode of the present invention, since a tape which retains an electrode element and is to be plastered on biological surface tissue is made of a flexible, extendable, and thin film, the tape can extend so as to follow the motion of the skin stemming from the movement of the subject, thereby preventing occurrence of inflammation in the skin.

What is claimed is:

1. A biomedical electrode comprising:

an electrode element having a conductive gel layer adhering to one end of the electrode element;

a tape retaining the other end of the electrode element and the tape adapted to be plastered on a biological surface tissue, the tape being made of a flexible, extendable, and thin film; and a reinforcing cover film for removably covering the side of the tape opposite the surface adapted to be plastered on the biological surface tissue, said reinforcing cover film being provided on the tape.

2. The biomedical electrode as defined in claim 1, wherein when the tape extends to a length which is twice the length of the tape when no tension is applied thereto, a force of 400 grams or less per 1 cm width is required.

3. The biomedical electrode as defined in claim 1, wherein the tape has a steam permeability of 400 $g/m^2/24$ hr or more.

4. The biomedical electrode as defined in claim 1, wherein the tape has a thickness of 0.1 mm or less.

5. The biomedical electrode as defined in claim 1, wherein the cover film is divided into two sub-sections, and butt faces of the two sub-sections are butt-joined, the portion of the cover film in the vicinity of the butt-joined portion is positioned without adhering to the tape.

6. The biomedical electrode as defined in claim 1, wherein a cut is formed in the cover film from its center to outer edge, and a tab tape for removing a cover film is attached to at least one side of the cover film with reference to the cut.

7. The biomedical electrode as defined in claim 1, wherein a tab tape for removing a cover film is attached to the outer edge of the cover film.

* * * * *

UNITED STATES PATENT AND TRADEMARK OFFICE
CERTIFICATE OF CORRECTION

PATENT NO. : 6,341,230 B1
DATED : January 22, 2002
INVENTOR(S) : Yasuaki Koike, Takayuki Kawasaki, Shigehiro Nishiwaki, Tadashi Matsumoto and Hideo Akita It is certified that error appears in the above-identified patent and that said Letters Patent is hereby corrected as shown below:

<u>Title page,</u>
Item [73], Assignees should read -- Nihon Kohden Corporation, Tokyo; Kabushikikaisya Kyowa, Osaka, both of (JP) --

Signed and Sealed this

Third Day of September, 2002

*Attest:*

JAMES E. ROGAN
*Attesting Officer*   *Director of the United States Patent and Trademark Office*